US00PP34124P2

(12) United States Plant Patent
Hochberg

(10) Patent No.: US PP34,124 P2
(45) Date of Patent: Apr. 12, 2022

(54) ***LAGERSTROEMIA* PLANT NAMED 'HOCH266'**

(50) Latin Name: *Lagerstroemia indica*
Varietal Denomination: HOCH266

(71) Applicant: Hochberg Ornamental Export Plants Ltd, Moshav Bitzaron (IL)

(72) Inventor: Omer Hochberg, Moshav Bitzaron (IL)

(73) Assignee: Hochberg Ornamental Export Plants Ltd

( * ) Notice: Subject to any disclaimer, the term of this patent is extended or adjusted under 35 U.S.C. 154(b) by 0 days.

(21) Appl. No.: 17/369,022

(22) Filed: Jul. 7, 2021

(51) Int. Cl.
*A01H 5/00* (2018.01)
*A01H 6/00* (2018.01)

(52) U.S. Cl.
USPC ..... Plt./252

(58) Field of Classification Search
USPC ..... Plt./252
See application file for complete search history.

*Primary Examiner* — Susan McCormick Ewoldt
(74) *Attorney, Agent, or Firm* — Cassandra Bright

(57) ABSTRACT

A new and distinct cultivar of *Lagerstroemia* plant named 'HOCH266' is disclosed, characterized by vivid red-purple flowers, and green foliage. Plants are dense and well-branched. The new variety is a *Lagerstroemia*, normally used for outdoor ornamental purposes.

1 Drawing Sheet

Latin name of the genus and species: *Lagerstroemia indica.*

Variety denomination: 'HOCH266'.

BACKGROUND OF THE INVENTION

The new *Lagerstroemia* cultivar is a product of a planned breeding program conducted by the inventor, in Moshav Bitzaron, Israel. The objective of the breeding program was to develop new Crepe Myrtle plants for ornamental purposes. The open pollination resulting in this new variety was made Jan. 7, 2014.

The seed parent is the unpatented proprietary variety referred to as *Lagerstroemia* 'L133'. The pollen parent is unidentified. The new variety was selected Oct. 8, 2015 by the inventor in a group of seedlings resulting from the 2014 open pollination, in a nursery in Moshav Bitzaron, Israel.

Asexual reproduction of the new cultivar was performed by fresh vegetative cuttings rooted under water mist. This was first performed at the same nursery in Moshav Bitzaron, Israel, Jan. 6, 2016, and has shown that the unique features of this cultivar are stable and reproduced true to type in multiple successive generations.

SUMMARY OF THE INVENTION

The cultivar 'HOCH266' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HOCH266' These characteristics in combination distinguish 'HOCH266' as a new and distinct *Lagerstroemia* cultivar:

1. Vivid red-purple blooms near RHS Red-Purple N74A.
2. Green foliage near RHS Green 139A with a slight marginal coloration near 187B.

3. Dense plant habit, reaching 40 to 60 cm in the second year.

PARENT COMPARISON

Plants of the new cultivar 'HOCH266' are similar to plants of the seed parent in most horticultural characteristics; however, plants of the new cultivar 'HOCH266' differ in the following:

1. The new variety has red-purple flowers, while the seed parent has purple flowers.

The pollen parent cannot be identified as the new variety is the result of an open pollination.

COMMERCIAL COMPARISON

Plants of the new cultivar 'HOCH266' are comparable to the commercial variety *Lagerstroemia* 'Purple Velvet', unpatented. The two *Lagerstroemia* varieties are similar in most horticultural characteristics, however, the new variety 'HOCH266' differs in the following:

1. The new variety has red-purple blooms; this comparator has purple blooms.
2. The new variety has larger, darker green leaves than this comparator.

Plants of the new cultivar 'HOCH266' are comparable to the commercial variety *Lagerstroemia* 'Whit VIII', U.S. Plant Pat. No. 16,616. The two *Lagerstroemia* varieties are similar in most horticultural characteristics; however, the new variety 'HOCH266' differs in the following:

1. The new variety has red-purple blooms, while this comparator has pink blooms.
2. The new variety has lighter green foliage than this comparator.

BRIEF DESCRIPTION OF THE PHOTOGRAPH

The accompanying photograph illustrates a typical flowering plant of 'HOCH266' grown outdoors in Moshav Bitzaron, Israel. The plant has been grown as a single stem, with a thick foliar and flowering head. Age of the plant is approximately 2 years. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 6$^{th}$ Edition 2015 except where general terms of ordinary dictionary significance are used. The following observations and measurements describe 'HOCH266' plants grown outdoors in Visalia, Calif. The growing temperature ranged from approximately 8° C. to 32° C. during the day and from approximately 1° C. to 12° C. during the night. General light conditions are normal sunlight and numerical values represent averages of typical plant types. Measurements were taken during June of 2020.

Botanical classification: *Lagerstroemia indica* 'HOCH266'.

PROPAGATION

Type of propagation typically used: Terminal vegetative cuttings.

Time to initiate roots: 14 to 21 days at about 24° c.

time to produce a rooted cutting: 28 to 35 days at about 24° C.

Root description: Very thin, fibrous, not fleshy, freely branching. New roots colored near RHS Yellow-White 158D. Older roots colored near Grey-Brown 199D.

PLANT

Age of plant described: 2 to 3 years old from a rooted cutting.

Container size: 3-gallon container.

Overall plant shape: Dense, erect.

Growth habit: Freely branching.

Plant spread: 50 cm.

Plant height: 60 to 65 cm in second year.

Growth rate: Moderate.

Plant vigor: Good.

Length of primary lateral branches: Varies as this is often pruned. 30 to 45 cm on average.

Diameter of lateral branches: 6 mm.

Quantity of lateral branches: About 6 main lateral branches, each with 2 to 4 branches.

Stem:

- *Color*.—New growth: Near RHS Greyed-Purple 187B, lightly streaked Yellow-Green 146D. Old growth: Near RHS Grey 201B streaked Grey-Brown 199B.
- *Shape*.—Round.
- *Strength*.—Good.
- *Aspect angle*.—Upright.
- *Texture*.—Very slightly scaly with age.

Internode length: Average range 1 to 2.1 cm.

Bark peel: Not observed.

FOLIAGE

Leaf:

- *Arrangement*.—Sub-opposite.
- *Average length*.—2.5 to 4 cm.
- *Average width*.—1.8 to 2.1 cm.
- *Shape of blade*.—Ovate.
- *Apex*.—Acute.
- *Base*.—Broad attenuate.
- *Margin*.—Entire. Occasionally very finely serrate.
- *Aspect*.—Undulate or upwardly folded.
- *Texture of top surface*.—Smooth.
- *Texture of bottom surface*.—Smooth.
- *Color*.—Young foliage upper side: Near RHS Green 139A. Marginal flush near Greyed-Purple 187A. Young foliage under side: Near RHS Green 137A, flushing around veins colored near 187B. Mature foliage upper side: Near RHS Green 139A. Thin marginal coloration near 187B. Mature foliage under side: Near RHS Yellow-Green 146B. Lightly flushed along margin and mid-vein Greyed-Purple 187B.
- *Venation*.—Type: Pinnate. Venation color upper side: Near RHS Yellow-Green 145B. Venation color under side: Near RHS Greyed-Yellow 160C.
- *Petiole*.—No petiole; sessile.

FLOWER

Natural flowering season: Begins flowering mid-June in California. Flowering continues until late August.

Inflorescence form: Panicles.

Flowers per inflorescence: About 200 to 350 flowers and buds.

Inflorescence size:

- *Width*.—23 cm.
- *Length*.—Average 17 cm.

Individual flowers:

- *Type*.—Rotate.
- *Shape*.—Obovate.
- *Habit*.—Whorled outward.
- *Diameter*.—3 cm.
- *Depth*.—1.5 cm.
- *Persistence*.—Self-cleaning.
- *Fragrance*.—Moderate fresh scent.

Petals:

- *Arrangement*.—Whorled.
- *Number*.—6.
- *Shape*.—Overall irregular orbicular.
- *Aspect*.—Deeply undulate.
- *Margin*.—Deeply ruffled, crenate.
- *Tip shape*.—Rounded.
- *Base shape*.—Rounded.
- *Length*.—1.0 cm, undulated, cannot unfold.
- *Width*.—1.2 cm, undulated, cannot unfold.
- *Texture*.—Upper: Glabrous. Lower: Glabrous.
- *Color*.—When opening: Upper surface: Near RHS Red-Purple N74A. Under surface: Near RHS Red-Purple N74A. Fully opened: Upper surface: Near RHS Red-Purple N74A. Under surface: Near RHS Red-Purple N74A.

Bud:

- *Shape*.—Sphere.
- *Length*.—7 mm.
- *Diameter*.—6 mm.
- *Color*.—Near RHS Greyed-Purple 187B.

Calyx:

- *Shape*.—Fused into a conical shape.
- *Length*.—9 mm.
- *Diameter*.—7 mm.

Sepals:

- *Appearance*.—Matte.
- *Arrangement*.—Rotate, fused.
- *Shape*.—Narrowly triangular.
- *Tip shape*.—Acute.

*Base shape*.—Obtuse.
*Margin*.—Entire.
*Quantity per flower*.—6.
*Length*.—9 mm.
*Width*.—3 mm.
*Margin*.—Entire.
*Texture*.—Inner: Smooth. Outer: Smooth.
*Color*.—Inner: Near RHS Yellow-Green 145C, margin flushed Greyed-Purple 187C. Outer: Near RHS Greyed-Purple 187C.

Peduncle:
*Length*.—Average range 1.5 cm.
*Diameter*.—5 mm.
*Texture*.—Glabrous.
*Color*.—Near RHS Greyed-Purple 187B.
*Orientation*.—Upright.
*Strength*.—Strong.

Pedicel:
*Length*.—5 to 6 mm.
*Diameter*.—1 to 2 mm.
*Angle*.—About 45° from attachment.
*Strength*.—Moderate.
*Texture*.—Slightly pubescent.
*Color*.—Near RHS Greyed-Purple 187A.

REPRODUCTIVE ORGANS

Stamens:
*Number*.—About 20, curled and congested.
*Filament length*.—About 6 mm, when pulled straight.
*Filament color*.—Near RHS White 155A.

Anthers:
*Shape*.—Ovate.
*Length*.—1 mm.
*Color*.—RHS Yellow 13A.
*Pollen*.—Not observed.

Pistil:
*Number*.—1.
*Length*.—1.6 cm.

Stigma:
*Shape*.—Globular.
*Color*.—Near RHS Red-Purple N66B.
*Ovary color*.—Near RHS Yellow 2D.

OTHER CHARACTERISTICS

Fruits and seeds: Not observed to date.

Disease/pest resistance: Observed resistance to mildew, assumed to be the pathogen *Erysiphe australiana*. Neither resistance nor susceptibility to other normal diseases and pests of *Lagerstroemia* observed.

Temperature range: Observed to tolerate a temperature range from −10° C. to 38° C.

What is claimed is:

1. A new and distinct cultivar of *Lagerstroemia* plant named 'HOCH266' as herein illustrated and described.

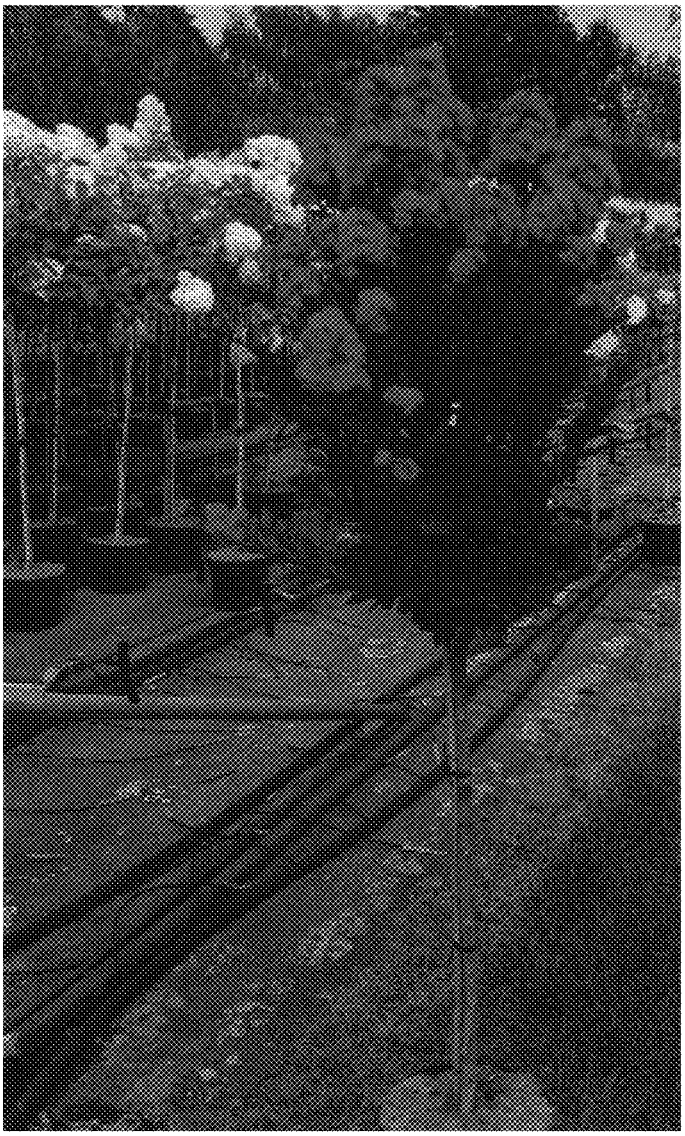

* * * * *